United States Patent [19]
Demachi

[11] Patent Number: 5,286,959
[45] Date of Patent: Feb. 15, 1994

[54] APPARATUS FOR READING AN IDENTIFICATION CODE FROM A SAMPLE CONTAINER AS IT IS ROTATED

[75] Inventor: Takashi Demachi, Kobe, Japan

[73] Assignee: Toa Medical Electronics Co., Ltd., Kobe, Japan

[21] Appl. No.: 747,665

[22] Filed: Aug. 20, 1991

[30] Foreign Application Priority Data

Oct. 5, 1990 [JP] Japan .............................. 2-105318[U]

[51] Int. Cl.$^5$ ........................ G06K 7/10; G01N 33/48
[52] U.S. Cl. .................................... 235/462; 422/62
[58] Field of Search .................... 235/462, 375; 422/62

[56] References Cited

U.S. PATENT DOCUMENTS 4,847,474  7/1989  Engel et al. .......................... 235/464
4,935,875  6/1990  Shah et al. ...................... 235/375 X

FOREIGN PATENT DOCUMENTS 57-199958  12/1982  Japan .
63-217273  9/1988  Japan .

Primary Examiner—Davis L. Willis
Assistant Examiner—Edward H. Sikorski
Attorney, Agent, or Firm—Thomas R. Morrison

[57] ABSTRACT

Apparatus for reading an identification code from a blood sample container includes an elastic member (42) which engages the upper side (34) of the sample container. A rotary device rotates the elastic member bidirectionally. An up-and-down moving device moves the elastic member up and down. A rotating/up-and-down moving control device (56) controls the movement of the container. An identification code reader (19) reads the sample code from the container, and a reading controller (57) permits the identification code reader to read from the container as it rotates in either forward or reverse direction. The elastic member abuts the upper part of the sample container and rotates it. If the identification code reader cannot read the identification code when the container rotates in the forward direction, the elastic member rotates the sample container in the reverse direction for the identification code to be read again.

2 Claims, 3 Drawing Sheets

APPARATUS FOR READING AN IDENTIFICATION CODE FROM A SAMPLE CONTAINER AS IT IS ROTATED

BACKGROUND OF THE INVENTION

The present invention relates to an identification code reader for a sample container for reading a sample identification code, such as a bar code attached to a sample container, when automatically supplying blood or other samples to a sample analyzer.

To prevent mistake in sampling, a bar code label or similar label for distinguishing it from others is glued to the outer wall of a sample container. The code marked on this label is read by a code reader installed in a blood analyzer or a smeared sample preparation unit.

If the sample container having the bar code label is merely set in the sample rack, the reading face of the bar code label may be directed to any side. But the code cannot be read unless the label is correctly facing the bar code reader.

There is prior art for eliminating reading error, for example, a device for reading a bar code while rotating the container as it is being lifted from the container supporting surface is disclosed in the Japanese Laid-open Patent Sho. 57-199958.

As far as the bar code label is glued neatly, by rotating the sample container, the bar code can be read regardless of the label position.

However, for example, when the edge of the label is slightly peeled, the peeled portion may be stuck in the sample rack when rotating, and the sample container cannot be rotated, and hence the bar code cannot be read.

OBJECTS AND SUMMARY OF THE INVENTION

It is a primary object of the invention to present a device capable of reading the code favorably regardless of the label position and even if the identification code label is not glued completely.

To achieve the above object, the invention presents, in a preferred embodiment thereof, an identification code reader for a sample container for reading a identification code of a sample container set up on a sample rack, with an identification code label glued on the outer wall thereof, comprising an elastic member disposed on the upper side of a sample container, rotary means for rotating the elastic member, up and down moving means for moving the elastic member up and down, rotating/up and down moving control means connected to the rotary means and up and down moving means, an identification code reader for reading the identification code of the sample container, and reading control means connected to the identification code reader for reading the identification code while rotating the sample container in any direction by abutting the elastic member to the upper part of the sample container.

In this apparatus, with the elastic member abutting against the upper part of the sample container, first by rotating in one direction, the identification code is read by the identification code reader. If it is not read, then the elastic member is rotated in the other direction to read the identification code again. This is achieved by the reading control means connected to the rotary means through the rotating/up and down moving control means.

In this apparatus, it is preferable to form the bottom of the elastic member in a circular form.

By the up and down moving means, the elastic member is moved toward the sample container to abut against its upper part. By the rotary means, the sample container rotates together with the elastic member. At this time, the identification code is read by the identification code reader. If the sample container is not rotated and the identification code cannot be read, it is rotated reversely to be read again. After reading, the elastic member stops rotating, and is removed from the sample container.

DETAILED DESCRIPTION OF THE PREFERRED EMBODIMENTS

Figure 3:
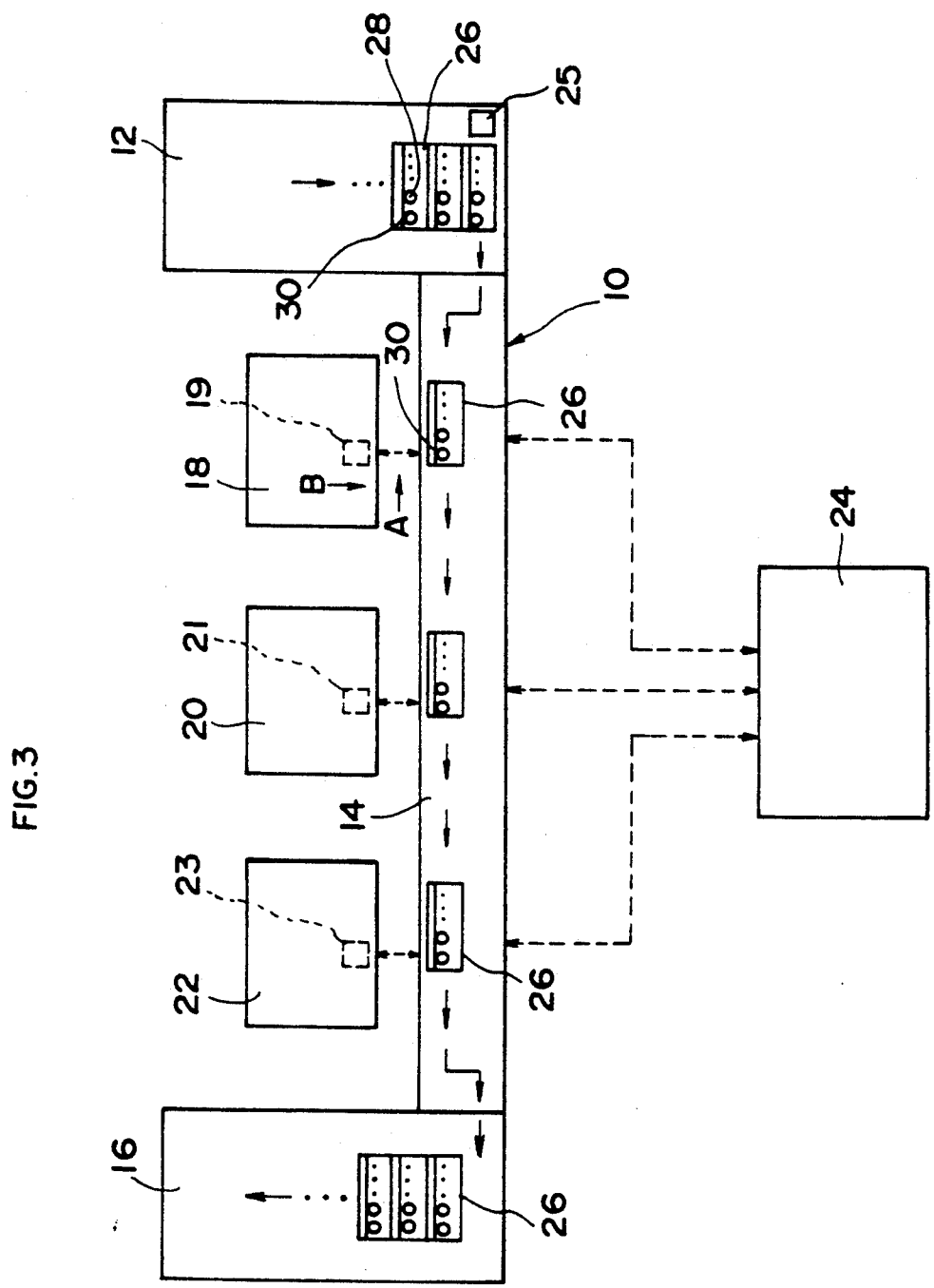
FIG. 3 is a schematic plan view showing an example of application of the apparatus of the invention in a comprehensive hematological examination system.

In FIG. 3, numeral 10 denotes rack transportation means of sample rack 26, and this rack transportation means 10 comprises a rack start unit 12, a conveyor unit 14, and a rack stock unit 16. Transportation is done, for example, by belt conveyor system. A sample rack 26 is shaped like a test tube stand for accommodating plural, for example, ten sample containers 28, and has an opening 30 at the rack side surface so that a bar code label 32 or similar label glued to the outer wall of the sample container 28 to distinguish it from others may be read from outside the rack. An example thereof is disclosed in the Japanese Laid-open Patent Sho. 63-217273. The sample container 28 may be used whether a plug 34 of the upper opening is detached or set in. The plug 34 is made of rubber or synthetic resin. It is hereinafter referred merely to as rubber plug 34. Anyway, the sample in the container 28 which may be stirred or sucked up by the known technology.

In the first place, the racks containing sample containers 28 are arranged in a parallel row in the rack start unit 12, and a start switch 25 is pushed. Then the racks 26 advance downward in FIG. 3, and the beginning rack 26 is sent out to the conveyor unit 14 at the left side. Numeral 24 is a controller.

Facing the conveyor unit 14, from the upstream to the downstream of the rack flow, there are disposed a blood analyzer 18 such as a blood corpuscle analyzer (e.g. model NE-8000 of Toa Medical Electronics), a blood analyzer 20 such as a reticulate red blood corpuscle analyzer (e.g. model R-1000 of Toa Medical Electronics), a smeared sample generator 22 (e.g. model SP-1 of Toa Medical Electronics), and others. The NE-8000 is a blood corpuscle analyzer capable of obtaining leukocyte data in five classifications, in addition to the conventional blood cell countings, the R-1000 is a reticulate red blood corpuscle analyzer for obtaining the reticulate red blood cell count and ratio, and the SP-1 is a smeared sample generator for preparing smeared samples of blood by the wedge method.

The rack conveyed in the conveyor unit 14 is first stopped before the blood analyzer 18.

Figure 1:
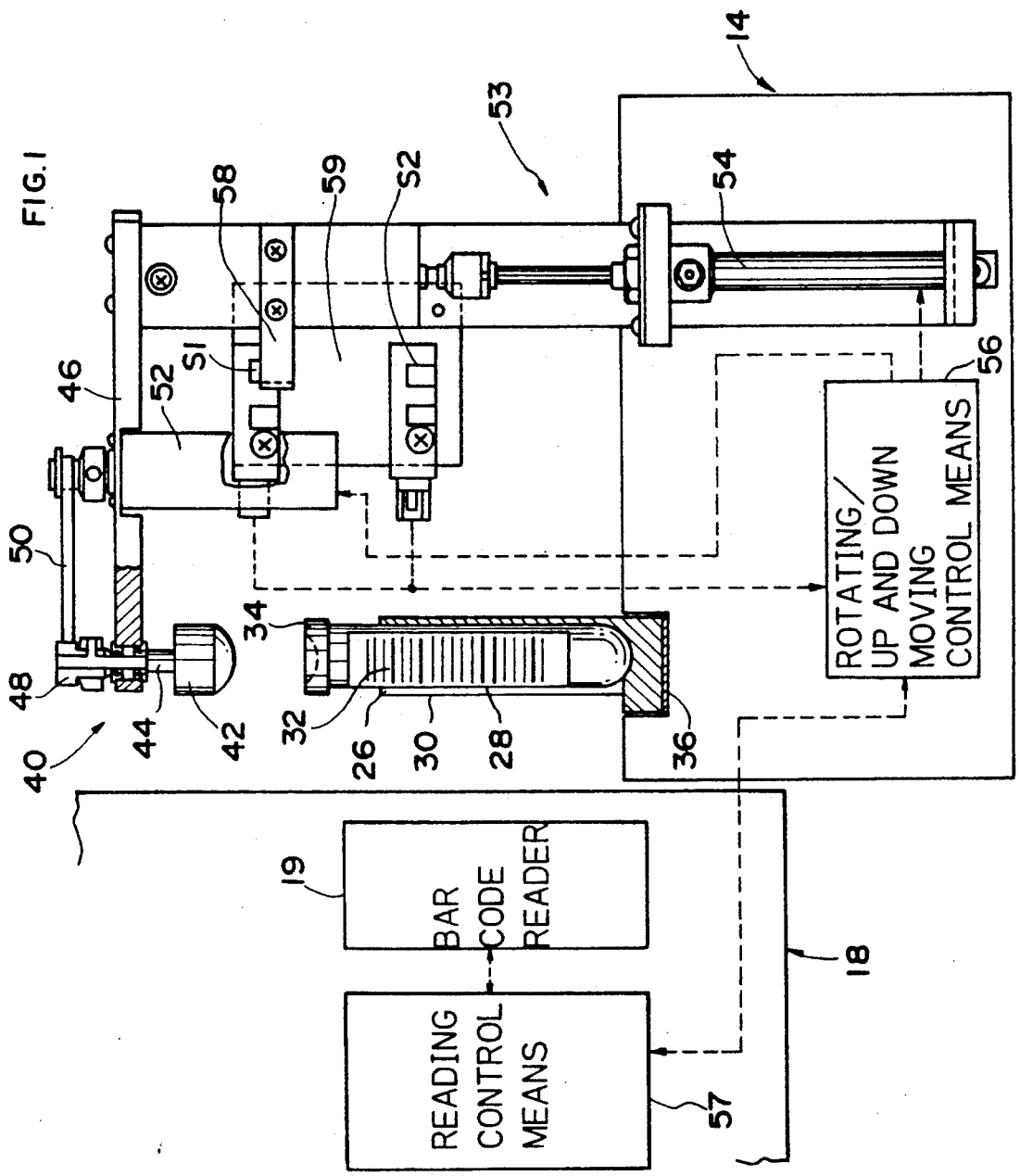
FIG. 1 is a side view showing an embodiment of a identification code reader for a sample container of the invention (as seen from the direction of arrow A in FIG. 3).
Figure 2:
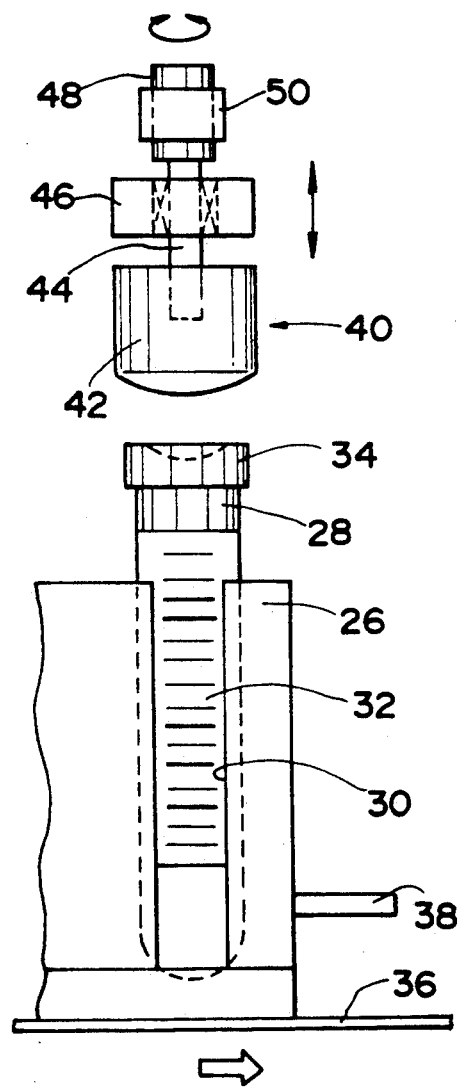
FIG. 2 is a magnified view around the sample container (as seen from the direction of arrow B in FIG. 3).

FIG. 1 shows an embodiment of the apparatus of the invention, which is a side view around the blood analyzer 18 and conveyor unit 14 (as seen from the direction of arrow A in FIG. 3). FIG. 2 is a magnified view around the sample container, observing the sample rack 26 on the conveyor unit from the blood analyzer 18 side (as seen from the direction of arrow B in FIG. 3). In this embodiment, the rubber plug is set in. If the rubber plug is removed, the bar code may be similarly read favorably.

The rack 26 coming in from the left side in FIG. 2, riding on a belt 36, abuts against, for example, a contact member 38, and is stopped at a specified position. By a bar code reader 19 incorporated in the front portion of the blood analyzer 18, a bar code label 32 of the sample container 28 is read, but the bar code label 32 is not always located at the same position. For example, the sample container 28 may be rotated during conveyance. Thus, if the bar code label 32 is not facing an opening 30 of the rack 26, the bar code label 32 cannot be read. It is therefore necessary to arrange to read the bar code label 32 wherever it may be located. For example, it may be read while rotating the sample container 28.

If, however, the label 32 is not glued correctly (for example, if the end of the label 32 is peeled off slightly or the label 32 is creased or projected), the label 32 may be caught in the sample rack 26, and the sample container 28 may not be rotated.

This problem may be solved by rotating the sample container 28 not only in the forward direction but also in the reverse direction.

Numeral 40 is an example of means for rotating the sample container. Numeral 42 is a columnar elastic member made of rubber or synthetic resin, slightly bulged in the bottom, and a shaft 44 is provided in the center of the elastic member. The shaft 44 is rotatably supported by a supporter 46 through a bearing. A pulley 48 is also fitted to the shaft 44, and a timing belt 50 is applied to the pulley 48, and the elastic member 42 is rotated by a driving source 52 such as a motor. A supporter 46 is designed to reciprocate linearly in the vertical direction by a driving source 54 such as an air cylinder. The driving sources 52, 54 are controlled by a rotating/up and down moving control means 56.

First, as the driving source 54 is put into action, the means for rotating 40 moves down, and the elastic member 42 abuts against the rubber plug 34 of the sample container 28. Next, the driving source 52 is put into action. Then the elastic member 42 begins to rotate slowly in one direction, while the sample container 28 also rotates slowly. The rotating speed is 30 to 60 rpm.

At this time, by a command from the reading control means 57, the bar code reader 19 reads the bar code label 32 of the rotating sample container 28. If the sample container 28 does not rotate and the bar code label 32 cannot be read, the driving source 52 is rotated in the reverse direction by the signal from the control means 57, 56, and the sample container 28 is rotated in the reverse direction. Then the bar code is read again.

Regardless of success or failure of bar code reading, it is also possible to read the bar code by rotating the driving source 52 in both normal and reverse directions.

If the bar code label 32 is not glued correctly, it may be possible to rotate it in the reverse direction even if it fails to rotate in the forward direction. The invention has been devised by taking notice of this point. Besides, by the rotation of the sample container 28, the imperfect glued portion of the bar code label 32 may be glued completely, corrected in the gap between the sample container 28 and the sample rack 26, which is another effect of the invention. Besides, the bottom of the elastic member 42 is formed approximately in an arc form. This is intended to raise the contact performance with the rubber plug 34 of the sample container 28 or the upper open end (without rubber plug 34) of the sample container 28, thereby decreasing uneven rotation.

Meanwhile, a light interrupting plate 58 and sensors S1, S2 (for example, photo interrupters) are monitoring the upward-downward motion of means for rotating 40. Usually, light interrupting plate 58 is located at the sensor S1 part, and while the elastic member 42 is abutting against the rubber plug 34 of the sample container 28, the light interrupting plate 58 is located between the sensor S1 and sensor S2. Without sample container 28, the light interrupting plate 58 is in the sensor S2 part, so that the presence or absence of the sample container may be judged. Thus, the bar code may be read easily and securely. Meanwhile, numeral 59 is a plate for mounting the sensors S1, S2.

After the bar code is read, as the contact member 38 moves to the right in FIG. 2 container 28 the width of one sample, the rack 26 also moves the width of one sample container 28, and sample container 28 is tumbled and stirred in a sample agitating part. The rack 26 is similarly sent transversely for the width of one sample, the agitated sample container 28 is taken out, and a sample is sucked out through the suction part having a thin tube shaped like a syringe needle. Then the blood corpuscles are analyzed. In this way, the rack 26 is intermittently sent sideways by one sample container 28, and similar processing is done sequentially. When processing of 10 sample containers, that is, one rack 26 is over, the rack 26 is further conveyed to the left in FIG. 3, and in the next blood analyzer 20, such as a reticulate red blood corpuscle analyzer, similarly, reading the bar code by bar code reader 21, agitation and suction of sample, and analysis are carried out sequentially.

Being thus composed, the invention brings about the following effects.

(1) If gluing of the bar code label is imperfect, the code may be read favorably regardless of the label position (2) When designed to rotate the sample container in a either direction, if the label is glued imperfectly, the sample container is rotated so that the bar code may be read securely.

(3) When the bottom of the elastic member is in a circular form, the contact of the sample container with the rubber plug or the upper open end of the sample container may be raised, so that uneven rotation may be reduced.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. Apparatus for reading an identification code of a container on a sample rack, said container having an identification code label attached on an outer wall thereof, said apparatus comprising:

an elastic member disposed on the upper side of said container;

means for rotating said elastic member;

means for moving said elastic member up and down;

first control means for controlling said rotary means and said up and down moving means;

an identification code reader for reading said identification code of said container;

second control means for controlling said identification code reader;

said means for rotating being effective for rotating said sample container first in a forward and then in a reverse direction by abutting said elastic member to an upper part of said container and rotating said elastic member;

whereby said identification code reader reads said identification code;

means for suppressing said rotating in said reverse direction when said identification code reader reads said identification code during said rotating in said forward direction;

a first sensor for detecting that said elastic member is located in a highest position;

said first sensor emitting a first output signal;

a second sensor for detecting that said elastic member is located in a lowest position;

said second sensor emitting a second output signal;

means for determining a one of the presence and absence of said sample container; and said means for determining being responsive to said first and said second output signal.

2. Apparatus for reading an identification code from a container as in claim 1, wherein a bottom of said elastic member is formed in a round shape.

* * * * *